United States Patent
Johnson

(10) Patent No.: US 11,660,086 B2
(45) Date of Patent: *May 30, 2023

(54) SURGICAL DEVICE WITH TRIGGER OPERATED NEEDLE

(71) Applicant: Arthrex, Inc., Naples, FL (US)

(72) Inventor: Matthew Johnson, Bonita Springs, FL (US)

(73) Assignee: Arthrex, Inc., Naples, FL (US)

( * ) Notice: Subject to any disclaimer, the term of this patent is extended or adjusted under 35 U.S.C. 154(b) by 58 days.

This patent is subject to a terminal disclaimer.

(21) Appl. No.: 17/350,009

(22) Filed: Jun. 17, 2021

(65) Prior Publication Data

US 2021/0307741 A1    Oct. 7, 2021

Related U.S. Application Data

(63) Continuation of application No. 16/401,634, filed on May 2, 2019, now Pat. No. 11,064,995.

(51) Int. Cl.
*A61B 17/04* (2006.01)
*A61B 17/062* (2006.01)
*A61B 17/00* (2006.01)

(52) U.S. Cl.
CPC ........ *A61B 17/0483* (2013.01); *A61B 17/062* (2013.01); *A61B 2017/00367* (2013.01)

(58) Field of Classification Search
CPC .............. A61B 17/0483; A61B 17/062; A61B 2017/00367; A61B 17/0469; A61B 17/0491; A61B 17/04; A61B 2017/0646; A61B 17/2909; A61B 17/0482; A61B 17/064; A61B 17/06061; A61M 25/09041; A61M 2025/09116; A61M 2025/09125; A61M 25/09; A61M 2025/09058

See application file for complete search history.

(56) References Cited

U.S. PATENT DOCUMENTS

| | | | |
|---|---|---|---|
| 6,030,393 A | 2/2000 | Corlew | |
| 8,460,318 B2 | 6/2013 | Murray et al. | |
| 10,028,736 B2 | 6/2018 | Shields et al. | |
| 11,064,995 B2 * | 7/2021 | Johnson | A61B 17/062 |

(Continued)

FOREIGN PATENT DOCUMENTS

EP    3326543 A1    5/2018

OTHER PUBLICATIONS

International Search Report and Written Opinion for International Application No. PCT/US2020/020734 dated Jun. 17, 2020.

*Primary Examiner* — Wade Miles
*Assistant Examiner* — Bridget E. Rabaglia
(74) *Attorney, Agent, or Firm* — Carlson, Gaskey & Olds, P.C.

(57) ABSTRACT

An exemplary surgical device includes a handle including a bore, and a trigger configured to advance or retract a needle through the bore of the handle. The trigger is configured to rotate about a pivot axis and is further configured to slide in distal and proximal directions. The device may be operated using one hand, and permits a user, such as a surgeon, to advance a needle through the device using intuitive, relatively easy thumb movements. While the device may be used in other techniques, it is particularly useful in meniscal repairs, including inside-out meniscal repairs.

20 Claims, 8 Drawing Sheets

(56) References Cited

U.S. PATENT DOCUMENTS

| | | |
|---|---|---|
| 2004/0243166 A1 | 12/2004 | Odermatt et al. |
| 2006/0069397 A1 | 3/2006 | Nobles et al. |
| 2009/0312792 A1 | 12/2009 | Fallin et al. |
| 2010/0130989 A1 | 5/2010 | Bourque et al. |
| 2012/0239062 A1 | 9/2012 | Saliman |
| 2016/0000422 A1 | 1/2016 | Harrison et al. |
| 2016/0000423 A1 | 1/2016 | Shields et al. |
| 2017/0325867 A1* | 11/2017 | Rapier .................. F16C 1/12 |
| 2018/0242968 A1 | 8/2018 | Mirochinik et al. |

* cited by examiner

SURGICAL DEVICE WITH TRIGGER OPERATED NEEDLE

RELATED APPLICATION(S)

This application is a continuation of prior U.S. application Ser. No. 16/401,634, filed May 2, 2019, the entirety of which is incorporated by reference herein.

BACKGROUND

This disclosure relates to a surgical device with a single trigger configured to rotate and slide. The disclosure also relates to a method of repairing damaged tissue.

Orthopedic procedures are often performed to repair musculoskeletal injuries, such as those sustained during sporting activities. Tears in the meniscus are known to be repaired by deploying suture on either side of the tear, tensioning the suture to close the tear, and allowing it to heal.

SUMMARY

This disclosure relates to a surgical device with a single (e.g., thumb) trigger configured to rotate and slide. The disclosure also relates to a method of repairing damaged tissue. A surgical device according to an exemplary aspect of the present disclosure includes, inter alia, a handle including a bore, and a trigger configured to advance or retract a needle through the bore of the handle. The trigger is configured to rotate about a pivot axis and further configured to slide in distal and proximal directions. The device may be operated using one hand, and permits a user, such as a surgeon, to advance a needle through the device using intuitive, relatively easy thumb movements. While the device may be used in other techniques, it is particularly useful in meniscal repairs, including inside-out meniscal repairs.

A surgical device according to an exemplary aspect of the present disclosure includes, inter alia, a handle including a bore, and a trigger configured to advance or retract a needle through the bore of the handle. The trigger is configured to rotate about a pivot axis and further configured to slide in distal and proximal directions.

A method according to an exemplary aspect of the present disclosure includes, inter alia, pressing on a trigger of a surgical device such that the trigger rotates into contact with a needle and moves in a distal direction to advance a needle within a bore of a handle of the surgical device.

DETAILED DESCRIPTION

Figure 1:
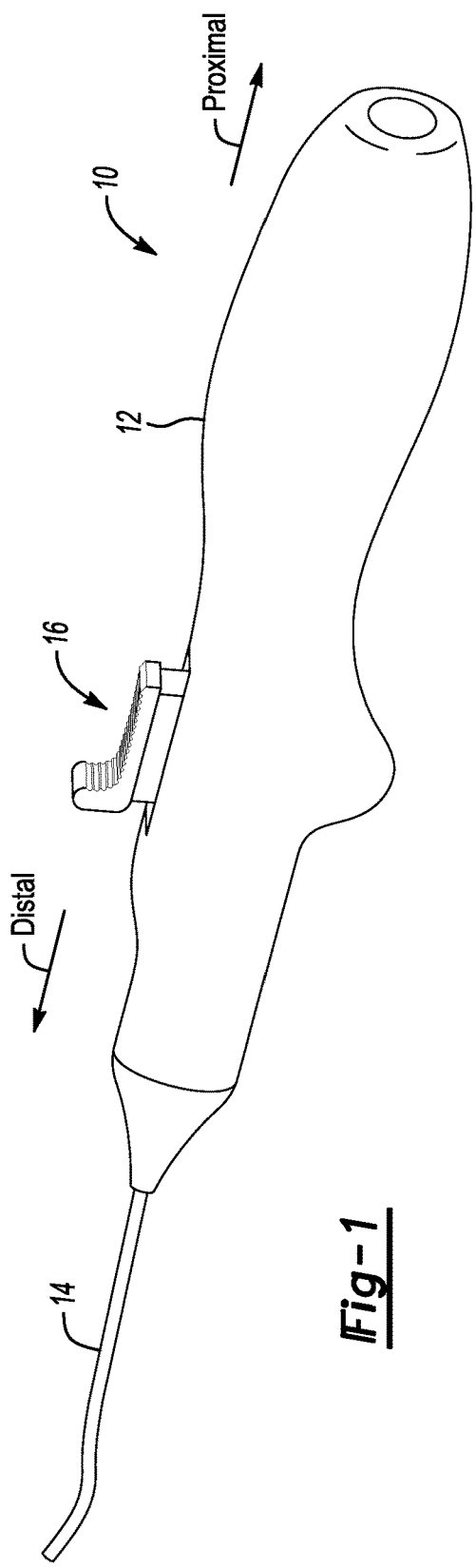
FIG. 1 illustrates an example surgical device.

This disclosure relates to a surgical device with a single trigger (e.g., a thumb trigger) configured to rotate and slide. The disclosure also relates to a method of repairing damaged tissue. A surgical device according to an exemplary aspect of the present disclosure includes, inter alia, a handle including a bore, and a trigger configured to advance or retract a needle through the bore of the handle. The trigger is configured to rotate about a pivot axis and further configured to slide in distal and proximal directions. The device may be operated using one hand, and permits a user, such as a surgeon, to advance a needle through the device using intuitive, relatively easy thumb movements. While the device may be used in other techniques, it is particularly useful in meniscal repairs, including inside-out meniscal repairs.

A surgical device according to an exemplary aspect of the present disclosure includes, inter alia, a handle including a bore, and a trigger configured to advance or retract a needle through the bore of the handle. The trigger is configured to rotate about a pivot axis and further configured to slide in distal and proximal directions.

In a further embodiment, the trigger is configured to rotate about the pivot axis between a first rotation position and a second rotation position, and the trigger is closer to a central axis of the bore of the handle in the second rotation position.

In a further embodiment, an inferior surface of the trigger is configured to contact the needle when the trigger is in the second rotation position.

In a further embodiment, an inferior surface of the trigger includes a channel, the trigger includes an insert projecting into the channel, and the insert is configured to contact the needle when the trigger is in the second rotation position.

In a further embodiment, the insert is made of a metallic material.

In a further embodiment, the surgical device includes a trigger assembly including the trigger, a trigger housing, and a pin. The trigger is configured to rotate relative to the trigger housing about the pin.

In a further embodiment, the pin defines the pivot axis perpendicular to a central axis of the bore of the handle.

In a further embodiment, the trigger housing includes a bore configured to permit the needle to move therethrough, the bore of the trigger housing coaxial with a central axis of the bore of the handle.

In a further embodiment, the trigger housing includes a channel extending from a superior surface of the trigger housing to the bore of the trigger housing, and a portion of the trigger is within the channel.

In a further embodiment, the trigger assembly includes a spring configured to bias the trigger away from a central axis of the bore of the handle.

In a further embodiment, the trigger assembly further includes a second pin received in a slot of the trigger, and the slot is shaped to limit the rotational movement of the trigger.

In a further embodiment, the entire trigger assembly is configured to slide relative to the handle in the distal and proximal directions.

In a further embodiment, the surgical device includes a spring configured to bias the trigger in the proximal direction.

In a further embodiment, the spring is a coil spring arranged about a central axis of the bore of the handle.

In a further embodiment, the surgical device includes a strand of suture including a first end connected to the needle and a second end connected to another needle.

In a further embodiment, a dimension of a superior surface of the trigger relative to a superior surface of the handle gradually increases distally.

In a further embodiment, the dimension of the superior surface of the trigger relative to the superior surface of the handle gradually increases distally until a tangent to the superior surface of the trigger is substantially perpendicular to a central axis of the bore.

A method according to an exemplary aspect of the present disclosure includes, inter alia, pressing on a trigger of a surgical device such that the trigger rotates into contact with a needle and moves in a distal direction to advance a needle within a bore of a handle of the surgical device.

In a further embodiment, the method includes reducing a force applied to the trigger such that the trigger rotates out of contact with the needle and moves in a proximal direction.

In a further embodiment, the method includes repeating the pressing and reducing steps to advance the needle through a meniscus.

FIG. 1 illustrates an example surgical device 10 according to the present disclosure. The surgical device 10 includes a handle 12 and a cannula 14 projecting distally (the "distal" direction is labeled in various figures for reference) from the handle 12. The handle 12 includes a trigger 16, which in this example is a thumb trigger. The trigger 16 is moveable in the distal and proximal directions (the "proximal" direction is labeled in various figures reference) to advance or retract a needle through the surgical device 10. In addition to being moveable in the distal and proximal directions, the trigger 16 is also rotatable to selectively grasp a needle such that distal movement of the trigger 16 advances the needle distally, for example, as will be explained in detail below.

Figure 2:
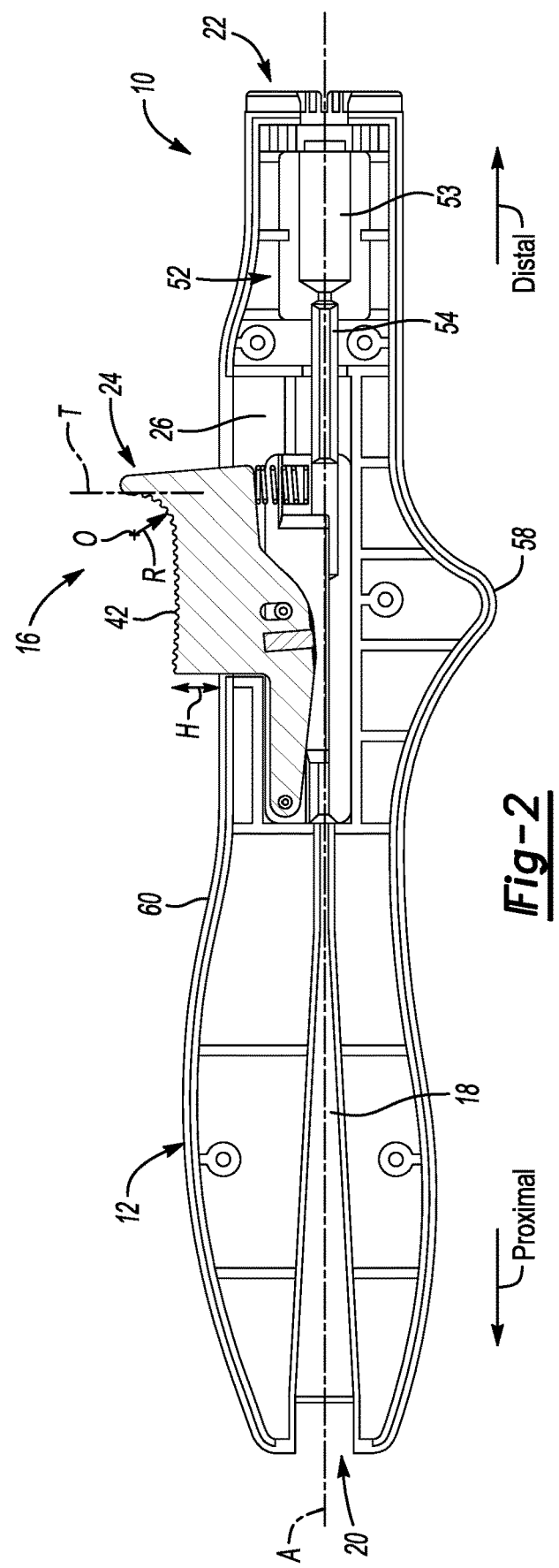
FIG. 2 is a cross-sectional view of a portion of the surgical device.
Figure 3:
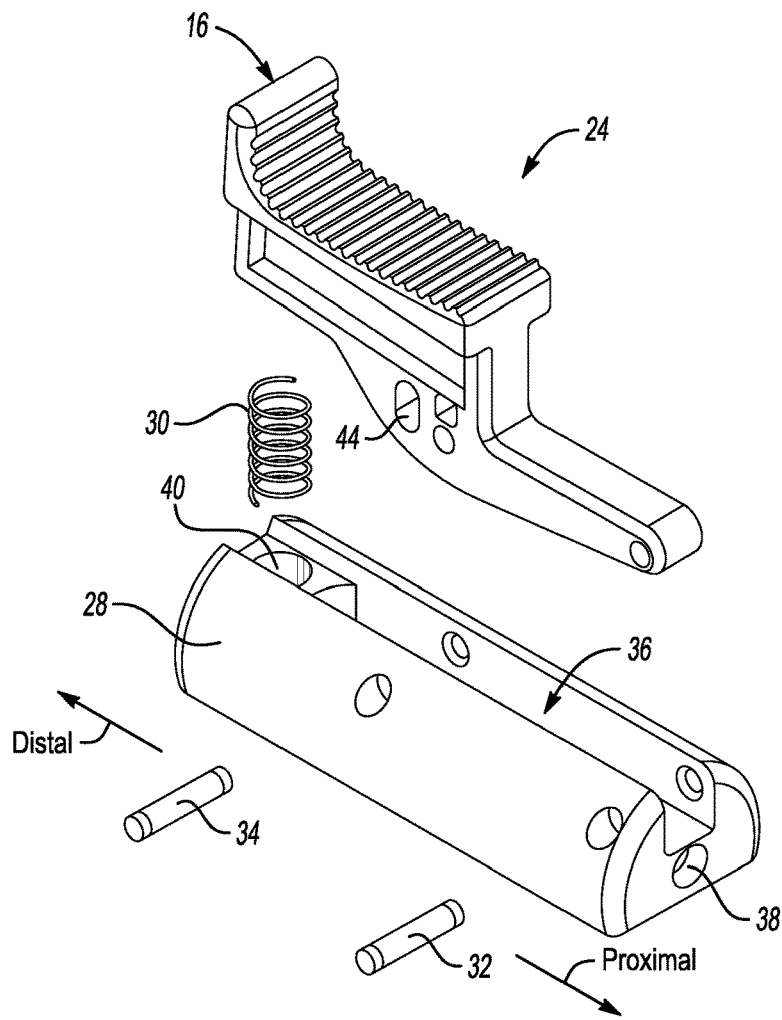
FIG. 3 is an exploded, perspective view of an example trigger assembly.
Figure 4:
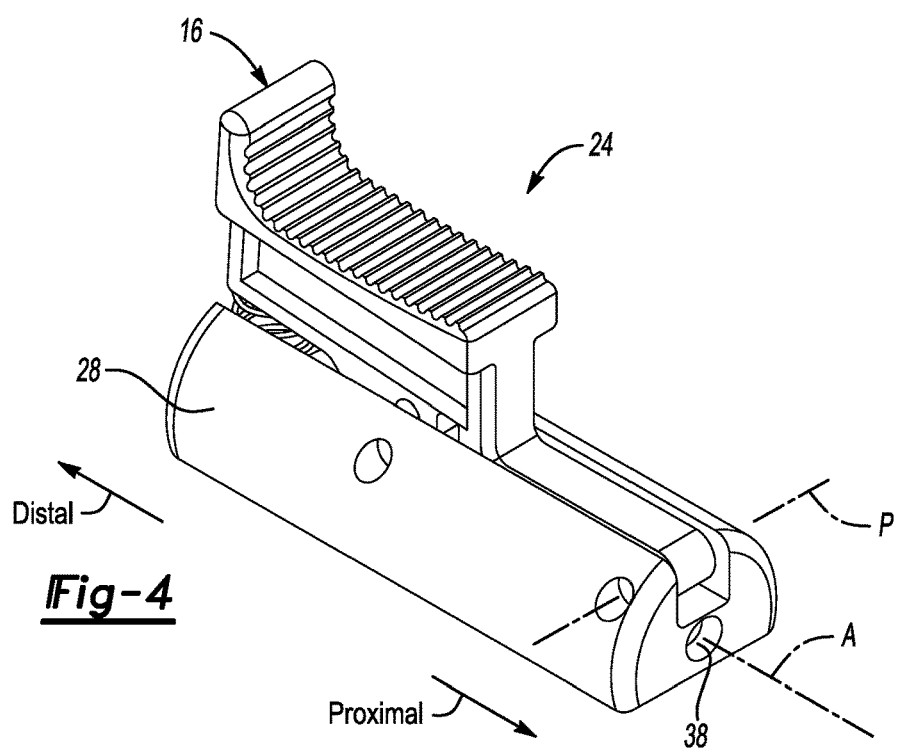
FIG. 4 is a perspective view of the trigger assembly.
Figure 5:
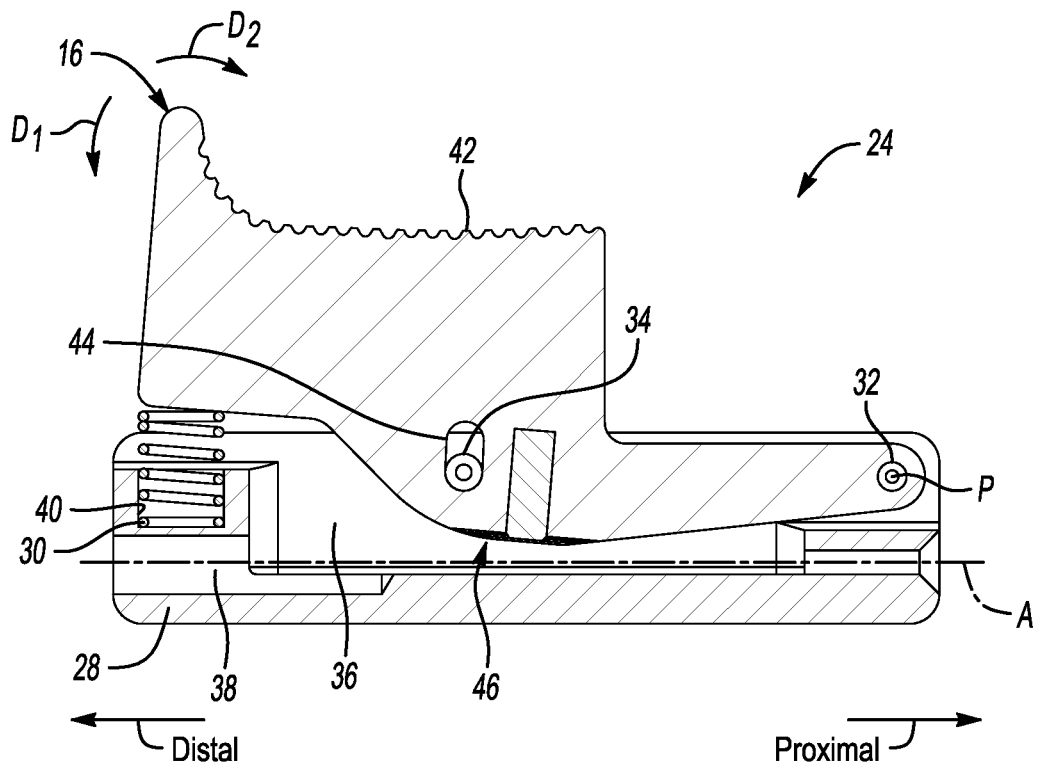
FIG. 5 is a cross-sectional view of the trigger assembly with a trigger in a first rotation position.

FIG. 2 is a cross-sectional view of the surgical device 10 with the cannula 14 removed for ease of reference. As shown in FIG. 2, the handle 12 includes a bore 18 extending along a central axis A. The bore 18 extends through the entirety of the handle 12, and in particular extends from a proximal end 20 of the handle 12 to a distal end 22 of the handle 12. The bore 18 is coaxial with a bore of the cannula 14 such that a needle advancing through the bore 18 is fed into the cannula 14. The bore 18 gradually widens adjacent the proximal end 20 of the handle 12 to facilitate loading of a needle.

The trigger 16 will now be described in more detail with reference to FIGS. 3-6. The surgical device 10 includes a trigger assembly 24, which is received in a recess 26 (FIG. 2) in the handle 12. The trigger assembly 24 includes a trigger housing 28, the trigger 16, a spring 30, a first pin 32, and a second pin 34. In this example, the spring 30 is a coil spring and the pins 32, 34 are cylindrical shafts. The trigger housing 28 includes a channel 36 extending from a superior surface of the trigger housing 28 and receiving a portion of the trigger 16. The trigger housing 28 further includes a bore 38 coaxial with the bore 18 of the handle 12. The channel 36 extends from the superior surface of the trigger housing 28 to the bore 38. The trigger housing 28 also includes a recess 40 receiving at least a portion of the spring 30.

Figure 6:
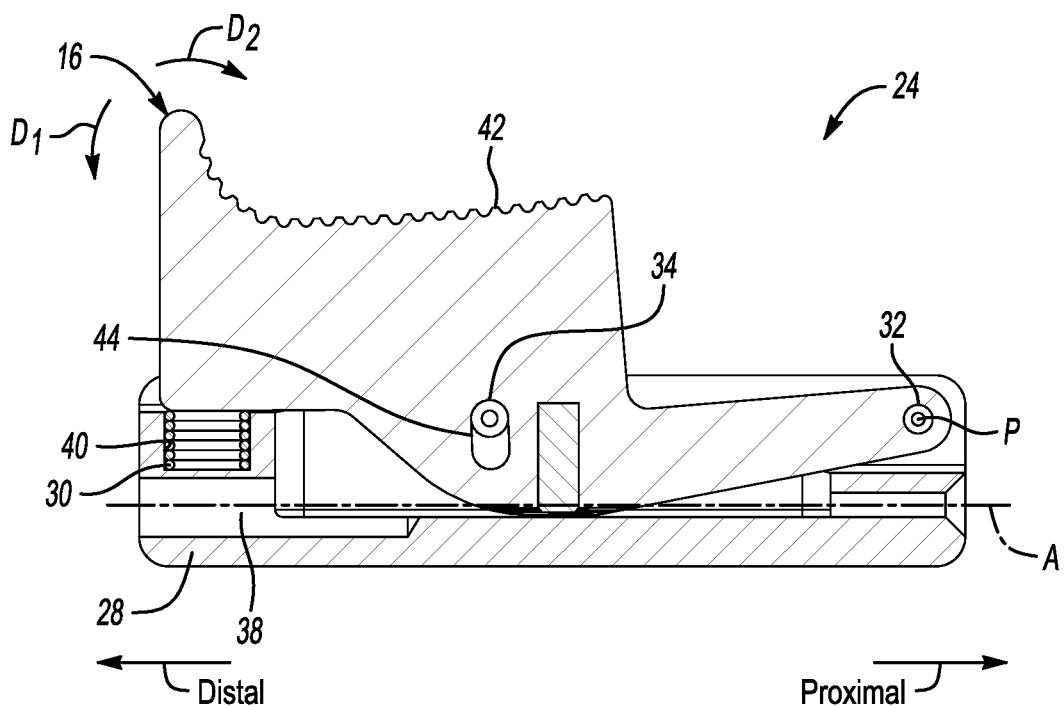
FIG. 6 is a cross-sectional view of the trigger assembly with the trigger in a second rotation position.

The trigger 16 is configured to rotate relative to the trigger housing 28 in first and second directions $D_1$, $D_2$ about a pivot axis P defined by the first pin 32. The spring 30 and recess 40 are arranged at a generally opposite end of the trigger housing 28 as the pivot axis P. The trigger 16 is configured to rotate about the pivot axis P between a first rotation position (FIG. 5) and a second rotation position (FIG. 6).

In order to move from the first rotation position to the second rotation position, a user, such as a surgeon, applies force using their a thumb, for example, to a superior surface 42 of the trigger 16, which causes the trigger 16 to rotate in direction $D_1$. The force applied by the surgeon overcomes a bias force applied by the spring 30 to the trigger 16 in the second direction $D_2$ and generally away from the central axis A. When in the second rotation position, the trigger 16 is closer to the central axis A of the bore 18 and the bore 38, which again are coaxial in this example.

Rotational movement of the trigger 16 relative to the trigger housing 28 is governed in part by a slot 44. The slot 44 is shaped so as to limit rotation of the trigger 16 in the directions $D_1$, $D_2$. In particular, the second pin 34 extends in a direction parallel to the pivot axis P through the slot 44. Contact between the pin 34 and the ends of the slot 44 restrict rotational movement of the trigger 16.

Figure 7:
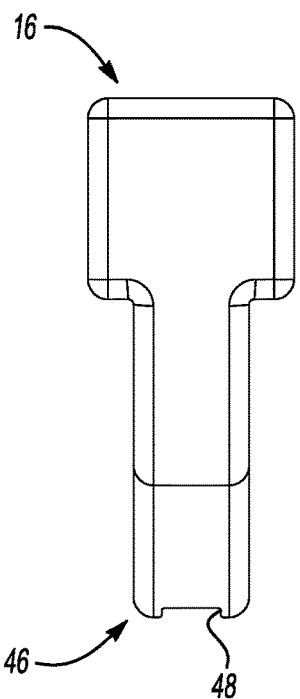
FIG. 7 is an end view of the trigger.

When in the second rotation position, the trigger 16 is configured to contact a needle within the bore 38 and hold the needle against the bore 38 such that distal or proximal movement of the trigger assembly 24 results in corresponding distal or proximal movement of the needle. An inferior surface 46 of the trigger 16 is configured to facilitate contact with the needle when the trigger is in the second rotation position. With specific reference to FIGS. 7 and 8, the inferior surface of the trigger 16 includes a channel 48 aligned with the central axis A and configured to guide a needle relative to the trigger 16. The channel 48 helps guide a needle within the bore 38. Further, the channel 48 is formed such that it is substantially flat and extends substantially parallel to the central axis A when the trigger 16 is in the second rotation position.

Figure 8:
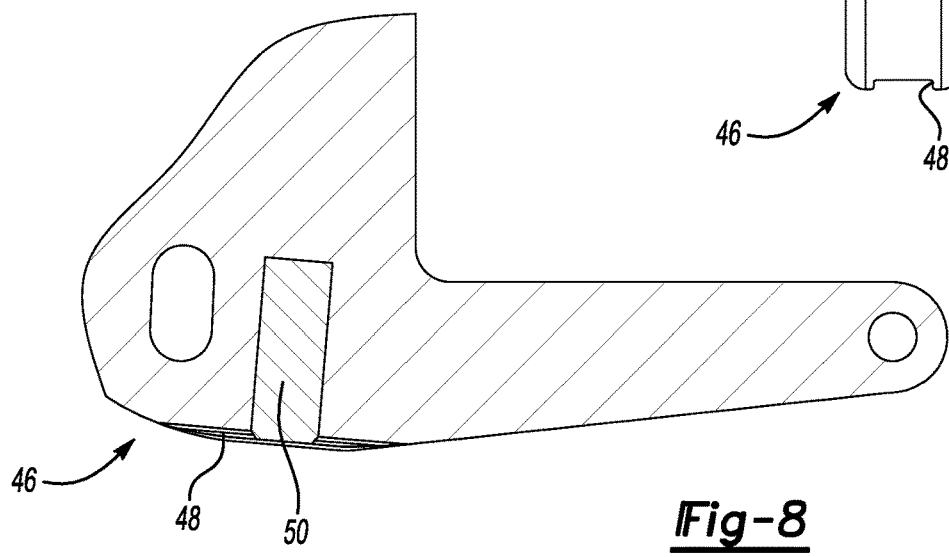
FIG. 8 is a partial cross-sectional view of the trigger.

An insert 50 (FIG. 8) within the trigger 16 projects into the channel 48 and is configured to contact a needle when the trigger 16 is in the second rotation position. In the example of FIG. 8, the insert 50 projects into the channel 48 but not beyond the inferior surface 46. This arrangement permits the insert 50 to contact a needle before the remainder of the trigger 16. The channel 48 is not required in all examples.

The insert 50 may be made of a material corresponding to the material of the needle. The insert 50 may also be made of a material different than the remainder of the trigger 16. In an example, the trigger 16 is made of a polymer material, and the insert 50 is made of a metallic material. Making the insert 50 of a metallic material increases the friction between the trigger 16 and the needle, which in turn increases the ease of advancing or retracting the needle.

Figure 9:
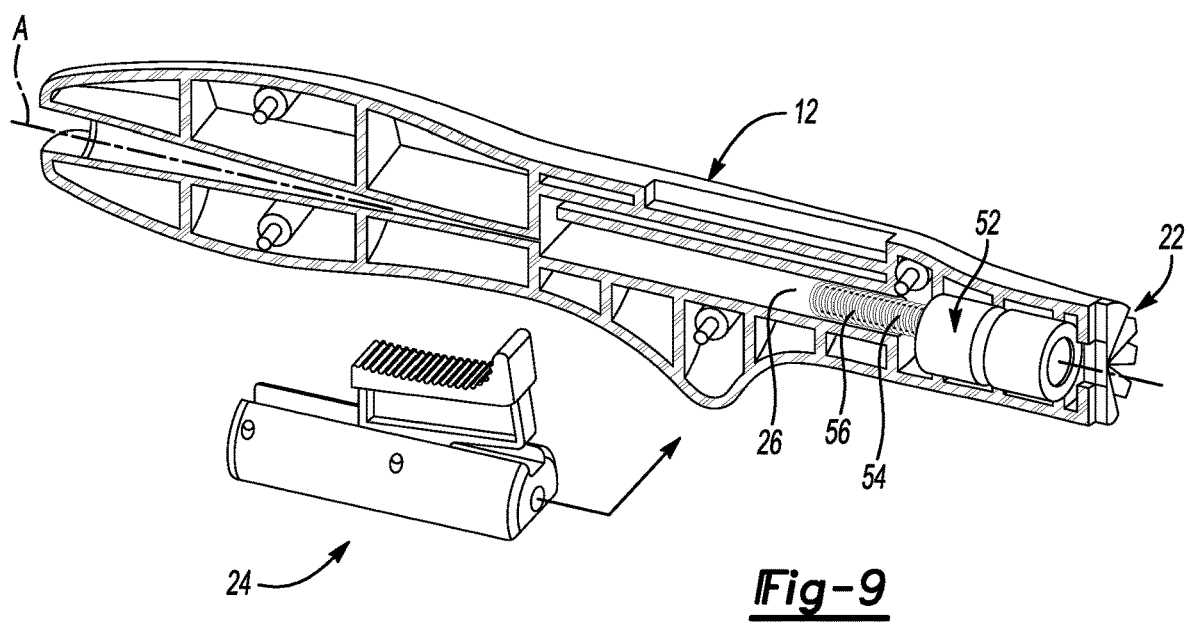
FIG. 9 is a partial cross-sectional view of the surgical device with the trigger assembly removed for reference.

In addition to the trigger assembly 24, the handle 12 includes a quick-connect fitting 52 adjacent the distal end 22 thereof. The quick connect fitting 52, which is shown in FIGS. 2 and 9, is configured to connect the cannula 14 to the handle 12 relatively quickly, by hand, and without the use of a tool. The quick connect fitting 52 includes a bore 53 (FIG. 2) coaxial with the bore 18 and allows a needle, for example, to pass therethrough. The quick connect fitting 52 permits a surgeon to conveniently select or change the cannula 14.

The quick connect fitting 52 in this example includes a shaft 54 (perhaps best seen in FIG. 2) projecting proximally toward the recess 26. A spring 56 is arranged about the shaft 54. The spring 56 is a coil spring and is arranged about the central axis A, in this example. The spring 56 is also in contact with the trigger assembly 24 and is configured to bias the trigger assembly 24 proximally. To this end, the entire trigger assembly 24 is configured to slide distally and proximally within the recess 26. The recess 26 is sized and shaped to limit the extent to which the trigger assembly 24 slides relative to the handle 12.

The surgical device 10 allows a surgeon to advance or retract surgical needles, such as meniscal repair needles, using one hand, and in particular using a smooth, intuitive thumb movement. When the surgeon grasps the handle 12, the surgeon's fingers rest comfortably adjacent a finger rest 58 (FIG. 2) on an inferior portion of the handle 12. In one example, the surgeon's index finger is distal of the finger rest 58 with the middle, ring, and pinky fingers proximal of the finger rest 58. The surgeon's thumb comfortably rests adjacent the trigger 16.

In order to advance a needle through the surgical device 10, the surgeon presses the trigger 16 down which pivots the trigger 16 into the second rotation position into contact with a needle, and then, while continuing to press the trigger 16 down, the surgeon slides the thumb actuator distally to advance the needle distally. The arrangement of the trigger 16 allows the surgeon to advance the needle by pressing down and forward in a single fluid movement. The surgeon then reduces the force applied to the trigger 16 by lifting their thumb off the trigger 16 or reducing the pressure they apply to the trigger 16, which causes the trigger 16 to disengage the needle under the force of spring 30 and slide proximally under the force of spring 56. The process is repeated to continue advancing the needle.

A number of repeated thumb movements may be required to fully advance a needle through the surgical device 10. The trigger 16 is suited to accommodate such movements. In particular, the superior surface 42 is wider than the remainder of the trigger 16 and projects above a superior surface of the handle 12. Specifically, in the first rotation position, as in FIG. 2, the superior surface 42 projects a height H above a superior surface 60 of the handle 12. Moving distally, the height H is substantially constant along a length of the trigger 16, except that, approaching a distal end portion of the trigger 16, the superior surface 42 curves away from the handle 12. In a particular example, the superior surface 42 adjacent a distal end portion of the trigger 16 is defined by a radius R having an origin O superior to the handle 12. The origin O extends perpendicular to the central axis A. The dimension H continually increases and follows the radius R, until a tangent T to the superior surface 42 is substantially normal to the central axis A. The arrangement of the superior surface 42 of the trigger 16 is particularly suited to a surgeon pressing the trigger 16 both distally and in the rotational direction $D_1$.

Figure 10:
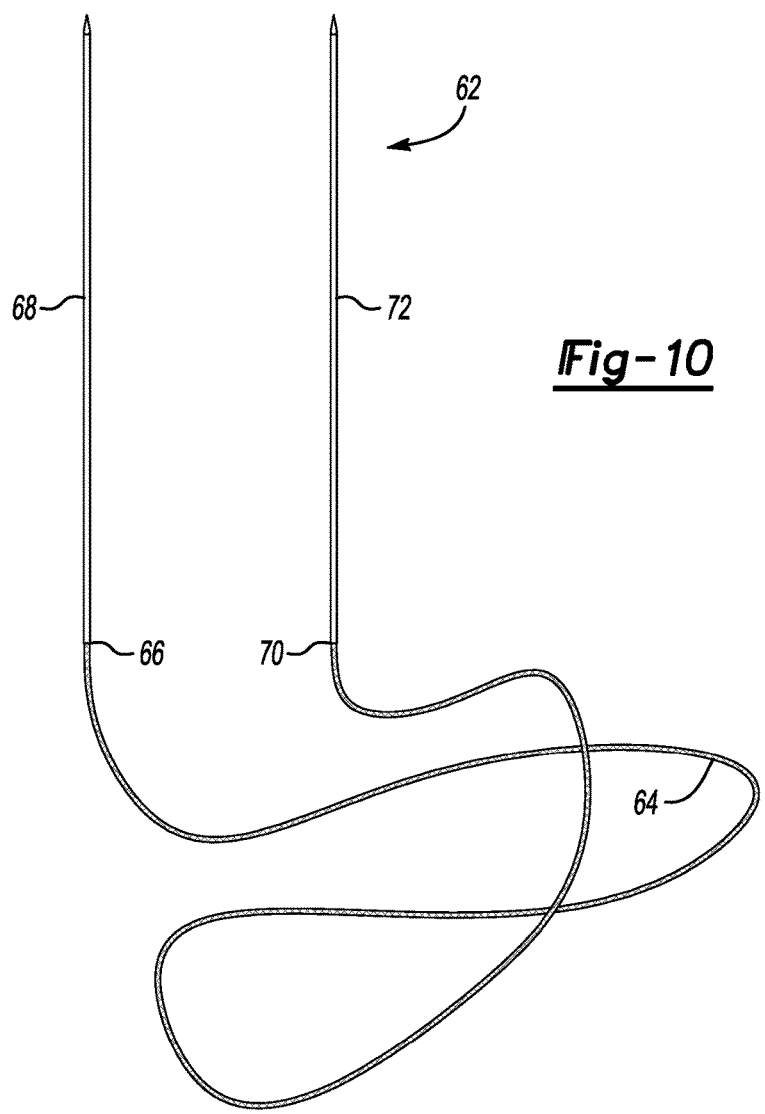
FIG. 10 illustrates an example construct.

FIG. 10 illustrates an example construct 62 configured to be used with the surgical device 10. The construct 62, in this example, includes a strand of suture 64 with a first end 66 connected to a first needle 68 and a second end 70 connected to a second needle 72. The first and second needles 68, 72 are configured to be advanced or retracted through the surgical device 10. The needles 68, 72 are metallic meniscal repair needles in this example.

The strand of suture 64 is provided by one of the following example types of suture: FiberWire®, TigerWire®, or FiberChain® suture, which are each available from Arthrex, Inc. It should be understood, however, that any type of suture may be used, including cored or coreless sutures. In another embodiment, the strand of suture 64 is flat suture, such as FiberTape® or SutureTape® suture, which are also available from Arthrex, Inc. The strand of suture 64 may also be a monofilament suture having barbs, as mentioned above. Further, the strand of suture 64 could include any soft, flexible strand of material, and is not limited to suture.

Figure 11:
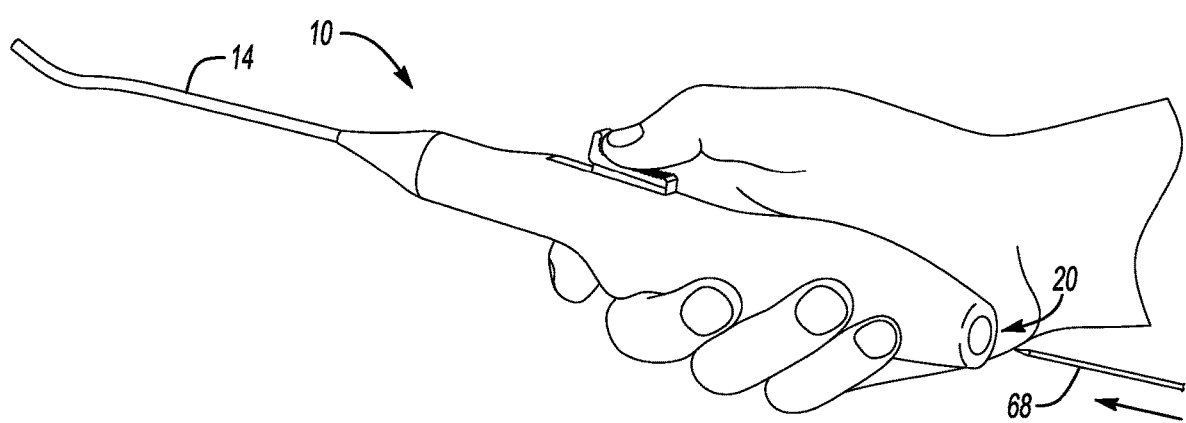
FIG. 11 illustrates a user loading a needle into the surgical device.

An example method of use will now be described. In FIG. 11, a surgeon grasps the surgical device 10 with one hand and loads the first needle 68 into the surgical device 10 by inserting it into the bore 18 at the proximal end 20 of the surgical device 10.

Figure 12:
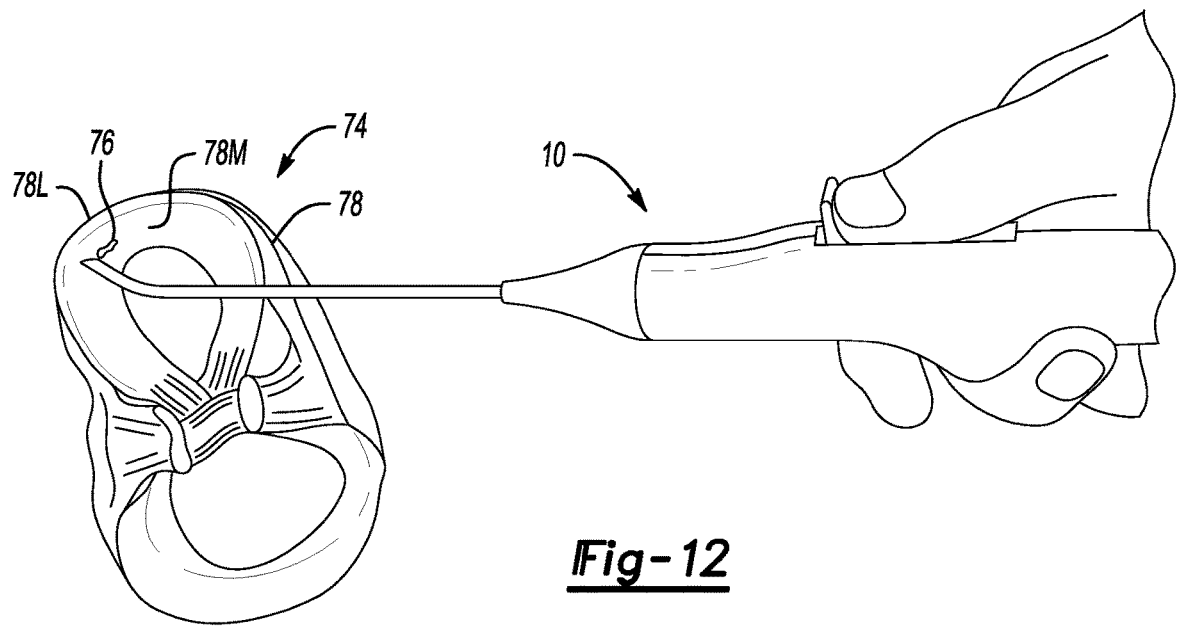
FIG. 12 illustrates the surgical device positioned adjacent a first side of a meniscal tear.

With reference to FIG. 12, the surgeon navigates the surgical device 10 within a joint space 74, such as a joint cavity in a knee, namely a cavity between a femur and a tibia. While a knee joint is illustrated, it should be understood that this disclosure extends to other joints. As illustrated in FIG. 12, there is a tear 76 in a meniscus 78. The meniscus includes 78 a medial surface 78M, or interior surface, and a lateral surface 78L, or exterior surface. The surgical device 10 is used to advance the needles 68, 72 through the meniscus 78 adjacent the tear 76, to deploy the suture 64 adjacent the tear 78 such that a surgeon can close the tear 78 and allow it to heal.

Figure 13:
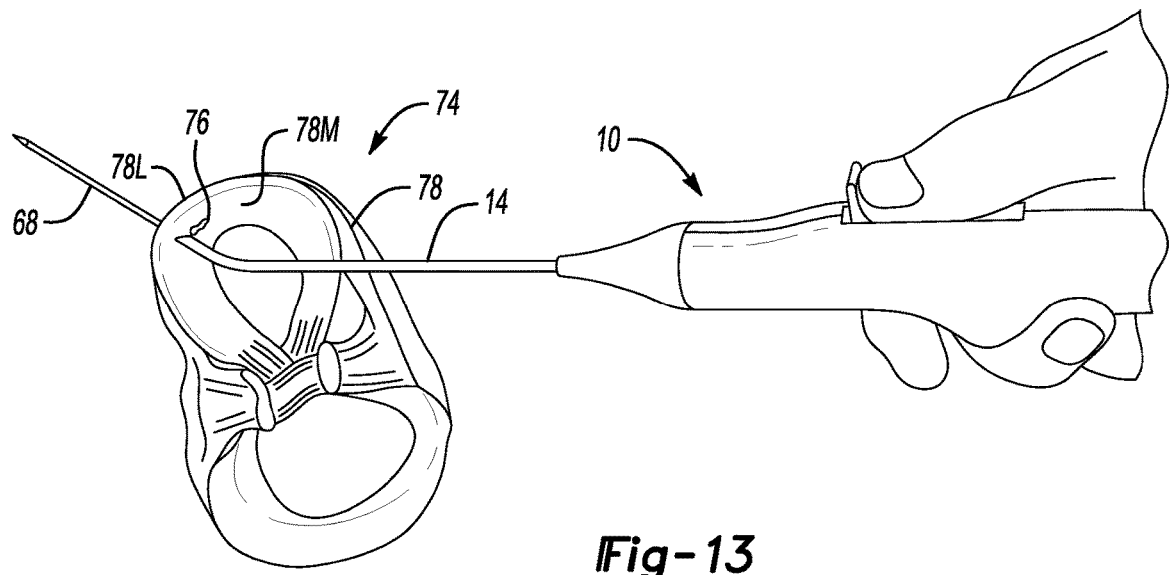
FIG. 13 illustrates a first needle passing through the meniscus.

In FIG. 13, with the cannula 14 placed adjacent the tear 76, the surgeon advances the first needle 68 through the meniscus 78 by pressing on the trigger 16 with his or her thumb, thereby causing the trigger 16 to rotate in direction $D_1$ and move distally, and then releasing the pressure applied to the trigger 16 to allow the trigger 16 to rotate back in direction $D_2$ and move proximally under the force of springs 30, 56. The surgeon repeats the pressing and releasing steps a number of times. Each time, the trigger 16 advances the first needle 68 further through the bore 18 until it exits the cannula 14 and penetrates through the meniscus 78. Once the first needle 68 projects sufficiently through the meniscus 78, the surgeon may pull the first needle 68 completely through the meniscus 78 using a tool, for example.

Figure 14:
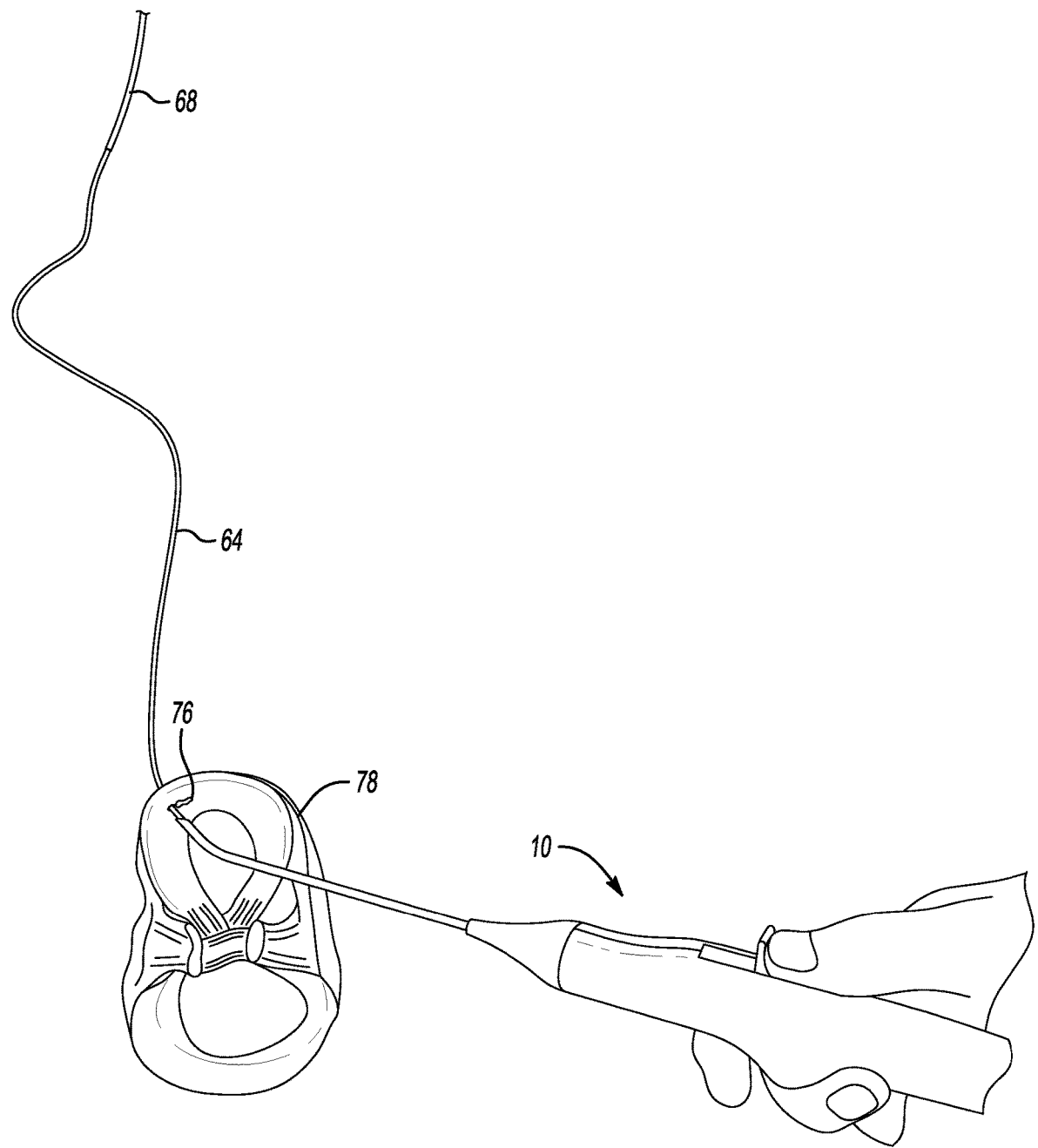
FIG. 14 illustrates a condition in which the first needle is fully passed through the meniscus.
Figure 15:
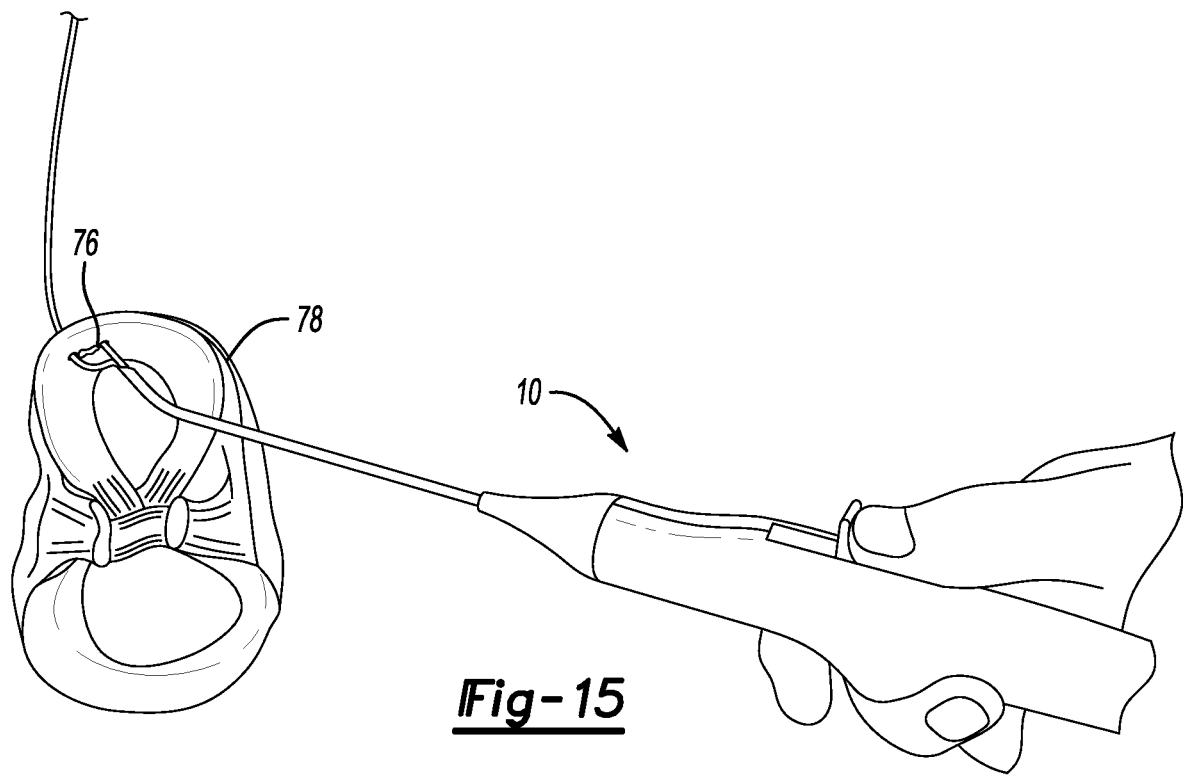
FIG. 15 illustrates the surgical device positioned adjacent a second side of a meniscal tear.
Figure 16:
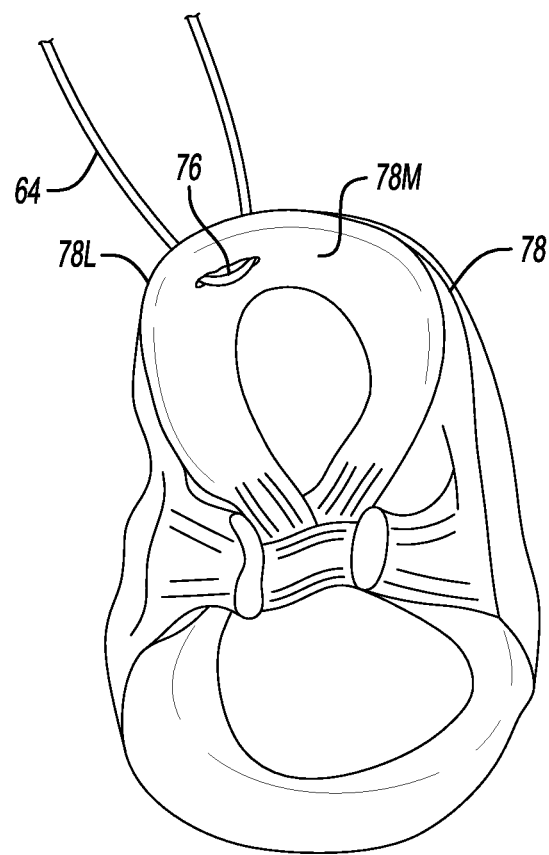
FIG. 16 illustrates a condition in which a second needle has fully passed through the meniscus.

FIG. 14 is representative of a condition where the first needle 68 has passed completely through the meniscus 78 such that the suture 64 passes through the meniscus 78 adjacent the tear 76. The surgeon then moves the surgical device 10 to another side of the tear 76, as shown in FIG. 15, and then surgeon loads the second needle 72 into the surgical device 10 and advances it through the meniscus 78 using trigger 16 according to the same process as described above. The surgeon then tensions both ends of the suture 64 to close the tear 76, as shown in FIG. 16. The surgeon may then use the suture 64 to tie a knot such that the knot abuts the lateral surface 78L. The process described relative to FIGS. 11-16 may be referred to as an inside out meniscal repair. The surgical device 10 may be used in other procedures, for example, and is not limited to use relative to the meniscus or the knee.

It should be understood that terms such as "lateral," "medial," "distal," "proximal," "superior," and "inferior" are used above consistent with the way those terms are used in the art. Further, these terms have been used herein for purposes of explanation, and should not be considered otherwise limiting. Terms such as "generally," "substantially," and "about" are not intended to be boundaryless terms, and should be interpreted consistent with the way one skilled in the art would interpret those terms.

Although the different examples have the specific components shown in the illustrations, embodiments of this disclosure are not limited to those particular combinations.

It is possible to use some of the components or features from one of the examples in combination with features or components from another one of the examples.

One of ordinary skill in this art would understand that the above-described embodiments are exemplary and non-limiting. That is, modifications of this disclosure would come within the scope of the claims. Accordingly, the following claims should be studied to determine their true scope and content.

The invention claimed is:

1. A surgical device, comprising:
    a handle including a bore; and
    a trigger configured to advance or retract a needle through the bore of the handle, wherein the trigger is configured to rotate about a pivot axis to selectively contact and disengage the needle, and wherein the trigger is further configured to slide in distal and proximal directions.

2. The surgical device as recited in claim 1, wherein:
    the trigger is configured to rotate about the pivot axis between a first rotation position and a second rotation position,
    the trigger is closer to a central axis of the bore of the handle in the second rotation position.

3. The surgical device as recited in claim 2, wherein an inferior surface of the trigger is configured to contact the needle when the trigger is in the second rotation position.

4. The surgical device as recited in claim 3, wherein:
    an inferior surface of the trigger includes a channel,
    the trigger includes an insert projecting into the channel, and
    the insert is configured to contact the needle when the trigger is in the second rotation position.

5. The surgical device as recited in claim 4, wherein the insert is made of a metallic material.

6. The surgical device as recited in claim 1, further comprising:
    a trigger assembly including the trigger, a trigger housing, and a pin, and wherein the trigger is configured to rotate relative to the trigger housing about the pin.

7. The surgical device as recited in claim 6, wherein the pin defines the pivot axis perpendicular to a central axis of the bore of the handle.

8. The surgical device as recited in claim 6, wherein the trigger housing includes a bore configured to permit the needle to move therethrough, the bore of the trigger housing coaxial with a central axis of the bore of the handle.

9. The surgical device as recited in claim 8, wherein:
    the trigger housing includes a channel extending from a superior surface of the trigger housing to the bore of the trigger housing, and
    a portion of the trigger is within the channel.

10. The surgical device as recited in claim 6, wherein the trigger assembly includes a spring configured to bias the trigger away from a central axis of the bore of the handle.

11. The surgical device as recited in claim 6, wherein:
    the trigger assembly further includes a second pin received in a slot of the trigger,
    the slot is shaped to limit the rotational movement of the trigger.

12. The surgical device as recited in claim 6, wherein the entire trigger assembly is configured to slide relative to the handle in the distal and proximal directions.

13. The surgical device as recited in claim 1, further comprising a spring configured to bias the trigger in the proximal direction.

14. The surgical device as recited in claim 13, wherein the spring is a coil spring arranged about a central axis of the bore of the handle.

15. The surgical device as recited in claim 1, further comprising a strand of suture including a first end connected to a first needle and a second end connected to a second needle.

16. The surgical device as recited in claim 1, wherein a dimension of a superior surface of the trigger relative to a superior surface of the handle gradually increases distally.

17. The surgical device as recited in claim 16, wherein the dimension of the superior surface of the trigger relative to the superior surface of the handle gradually increases distally until a tangent to the superior surface of the trigger is substantially perpendicular to a central axis of the bore.

18. A method, comprising:
    pressing on a trigger of a surgical device such that the trigger rotates from a first rotation position in which the trigger is disengaged from a needle to a second rotation position in which the trigger contacts with the needle, and wherein the pressing step further includes, when the trigger is in the second rotation position, moving the trigger in a distal direction to advance the needle within a bore of a handle of the surgical device.

19. The method as recited in claim 18, further comprising:
    reducing a force applied to the trigger such that the trigger rotates to the first rotation position, disengages the needle, and moves in a proximal direction.

20. The method as recited in claim 19, further comprising:
    repeating the pressing and reducing steps to advance the needle through a meniscus.

* * * * *